United States Patent
Khayyat et al.

(10) Patent No.: US 9,707,203 B1
(45) Date of Patent: Jul. 18, 2017

(54) METHODS OF KILLING BACTERIA AND PREVENTING OR TREATING BACTERIAL INFECTION WITH OXIDATION PRODUCTS OF SAFRANAL AND METHODS OF SYNTHESIZING SAFRANAL EPOXIDES

(71) Applicant: King Abdulaziz University, Jeddah (SA)

(72) Inventors: Suzan Abdulrahman I. Khayyat, Jeddah (SA); Eman Mahmoud Ibraheem Elgendy, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 15/289,659

(22) Filed: Oct. 10, 2016

(51) Int. Cl.
| | | |
|---|---|---|
| C07D 301/14 | (2006.01) | |
| C07D 493/04 | (2006.01) | |
| A61K 31/336 | (2006.01) | |
| A01N 43/20 | (2006.01) | |
| A01N 43/90 | (2006.01) | |
| A61K 45/06 | (2006.01) | |

(52) U.S. Cl.
CPC .......... *A61K 31/336* (2013.01); *A01N 43/20* (2013.01); *A01N 43/90* (2013.01); *A61K 45/06* (2013.01); *C07D 301/14* (2013.01); *C07D 493/04* (2013.01)

(58) Field of Classification Search
CPC .. C07D 301/14; C07D 493/04; A61K 31/336; A61K 45/06; A01N 43/20; A01N 43/90
USPC .................. 514/475; 468/420, 446
See application file for complete search history.

(56) References Cited

FOREIGN PATENT DOCUMENTS

AU        2005229753 A1      5/2007

OTHER PUBLICATIONS

Corma et al Arkivoc, 2005 ix 124-132.*
S.Muzaffar., et al., "In vitro bactericidal and fungicidal activities of various extracts of saffron (*Crocus sativus* L.) stigmas from Jammu & Kashmir, India" Muzaffar et al., Cogent Food & Agriculture(2016), 2: 1158999, pp. 1-7.
H. Motamedi, et al., "In vitro assay for the anti-brucella activity of medicinal plants against tetracycline-resistant *Brucella melitensis*" Journal of Zhejiang Univeristy—Science B (Biomedicine & Biotechnology), 2010, pp. 506-511.
M. Teimouri, "The Chemical Composition and Antimicrobial Activity of Essential Oils of *Vaccinium arctostaphylos* L." International Journal of Advanced Biological and Biomedical Research, 2014; 2 (11), pp. 2837-2841.
C. Pintado, et al., "Bactericidal effect of saffron (*Crocus sativus* L.) on *Salmonella enterica* during storage" Food Control, vol. 22, Issues 3-4, Mar.-Apr. 2011,2010, pp. 638-642.
R.Rezaee, et al., "Safranal: From an Aromatic Natural Product to a Rewarding Pharmacological Agent" Iranian Journal of Basic Medical Sciences, vol. 16 No. 1, Jan. 2013, pp. 12-26.

* cited by examiner

*Primary Examiner* — Yevegeny Valenrod
(74) *Attorney, Agent, or Firm* — Oblon, McClelland, Maier & Neustadt, L.L.P.

(57) ABSTRACT

A method of killing bacteria. The method includes contacting the bacteria with an effective amount of at least one oxidation product of safranal selected from the group consisting of a compound of formula II, a compound of formula III, and stereoisomers thereof.

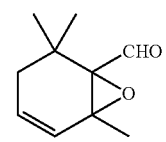

(II)

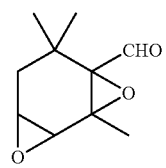

(III)

The oxidation products of safranal of formula II and/or formula III are preferably synthesized by subjecting safranal to oxidation reactions either photochemically with at least one peroxide in the presence of light or thermally with at least one organic peracid.

2 Claims, 4 Drawing Sheets

METHODS OF KILLING BACTERIA AND PREVENTING OR TREATING BACTERIAL INFECTION WITH OXIDATION PRODUCTS OF SAFRANAL AND METHODS OF SYNTHESIZING SAFRANAL EPOXIDES

BACKGROUND OF THE INVENTION

Technical Field

The present disclosure relates to methods of killing bacteria and methods of preventing or treating bacterial infection in a human or an animal. More specifically, the present disclosure relates to methods of killing bacteria and methods of preventing or treating bacterial infection using oxidation products of safranal, preferably safranal epoxides.

The present disclosure also relates to methods of synthesizing safranal epoxides thermally and photochemically.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, is neither expressly nor impliedly admitted as prior art against the present invention.

Safranal (2,6,6-trimethyl-1,3-cyclohexadiene-1-carboxaldehyde) is a naturally occurring compound present in *Crocus sativus* L. (saffron) (Fam. Iridaceae), a plant cultivated to make saffron spice. Saffron spice has been used in seasoning, medicine, cosmetics, perfume and dye for over three millennia. Due to its volatility, safranal is responsible for the aroma of saffron.

Antibiotics have been used for the treatment of bacterial infections for a long time. As a result, antibiotic resistance, particularly among pathogenic bacteria, is on the rise.

It is an object of this disclosure to provide methods of killing bacteria, particularly bacteria resistant to antibiotics, methods of preventing or treating bacterial infections with oxidation products of safranal, preferably safranal epoxides, and methods of synthesizing safranal epoxides.

BRIEF SUMMARY OF THE INVENTION

According to a first aspect, the present disclosure relates to a method of killing bacteria.

In one embodiment, the method includes contacting the bacteria with an effective amount of safranal of formula (1).

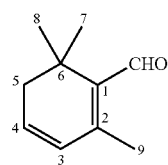

In another embodiment, the method includes contacting the bacteria with an effective amount of at least one oxidation product of safranal selected from the group consisting of a compound of formula II, a compound of formula III, and stereoisomers thereof.

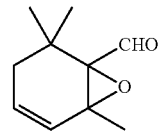

(II)

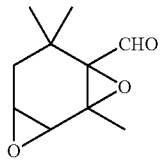

(III)

In one or more embodiments, the compound of formula II and/or the compound of formula III are synthesized by reacting safranal with at least one organic peracid, preferably thermally at a temperature of, e.g. 15-35° C., or 20-30° C.

In a preferred embodiment, the organic peracid is m-chloroperbenzoic acid. A probable mechanism for the formation of the oxidation products of safranal of formula II and III is believed to involve one oxirane intermediate (A) and elimination of m-chlorobenzoic acid molecule to form the product of formula II or two oxirane intermediates (A and B) to form the product of formula III.

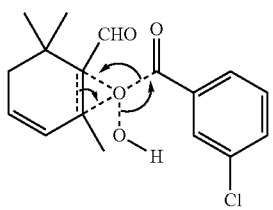

(A)

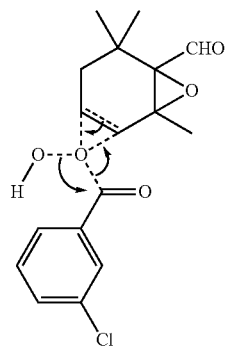

(B)

In one or more embodiments, the compound of formula II and/or the compound of formula III are synthesized by reacting safranal with at least one peroxide photochemically in the presence of light.

In one or more embodiments, the bacteria are at least one selected from the group consisting of bacteria of the genus *Proteus*, bacteria of the genus *Klebsiella*, bacteria of the genus *Bacillus*, bacteria of the genus *Pseudomonas*, bacteria of the genus *Staphylococcus*, bacteria of the genus *Escherichia*, bacteria of the genus *Brucella*, and bacteria of the genus *Salmonella*.

In one or more embodiments, the bacteria are resistant to at least one antibiotic selected from the group consisting of a beta-lactam antibiotic, a tetracycline, a colistin, and a vancomycin.

In one or more embodiments, the beta-lactam antibiotic is selected from the group consisting of a methicillin, an oxacillin, a nafcillin, a penicillin, a cephamycin, a carbapenemtetracycline, and any combination thereof.

In one or more embodiments, the bacteria are present in a liquid or a solid medium, and the effective amount of the at least one oxidation product of safranal lies in the range of 0.1-100 mg/ml liquid or solid medium.

In one or more embodiments, the method further comprises contacting the bacteria with at least one antibiotic concurrently with the contacting of the bacteria with the at least one oxidation product of safranal, and the at least one antibiotic is selected from the group consisting of a methicillin, an oxacillin, a nafcillin, a penicillin, a cephamycin, a carbapenemtetracycline, a cephalosporin, a carbepenem, other beta-lactam antibiotics, a tetracycline, a colistin, a vancomycin, an aminoglycoside, an amphenicol, an ansamycin, a macrolide, a lincosamide, a glycopeptide, a polypeptide, a chloramphenicol, a quinolone, a fucidin, a sulfonamide, a sulfone, a nitrofuran, a diaminopyrimidine, a trimethoprim, a rifamycin, a streptogramin, a lipopeptide, a ketolide, a polyene, an azole, an echinocandin, and any combination thereof.

According to a second aspect, the present disclosure relates to a method of preventing or treating an infection of bacteria in a subject who is suffering from or susceptible to bacterial infection. The method includes administering to the subject an effective amount of a composition comprising at least one oxidation product of safranal selected from the group consisting of a compound of formula II, a compound of formula III, and stereoisomers thereof to prevent, inhibit, or reduce a growth of the bacteria.

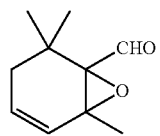
(II)

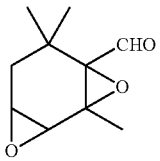
(III)

In a preferred embodiment, the oxidation products of safranal of formula II and III are synthesized by reacting safranal with m-chloroperbenzoic acid. A probable mechanism for the formation of the oxidation products of safranal of formula II and III is believed to involve one oxirane intermediate (A) and elimination of m-chlorobenzoic acid molecule to form the product of formula II or two oxirane intermediates (A and B) to form the product of formula III.

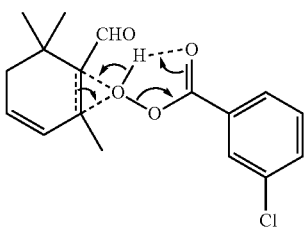
(A)

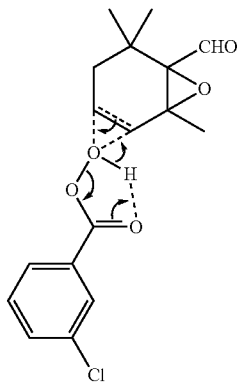
(B)

In one or more embodiments, the composition further comprises at least one pharmaceutically, cosmetically, and/or dietarily acceptable excipient or carrier.

In one or more embodiments, the composition is in a form selected from the group consisting of a solution, a spray, a beverage, a tablet, a gel, a paste, a lotion, a cream, a capsule, a powder, and a lozenge.

In one or more embodiments, the composition is administered intravenously, intradermally, intraperitoneally, orally, by inhalation, transdermally (topical), subcutaneously, and/or transmucosally.

In one or more embodiments, the bacteria are at least one selected from the group consisting of bacteria of the genus *Proteus*, bacteria of the genus *Klebsiella*, bacteria of the genus *Bacillus*, bacteria of the genus *Pseudomonas*, bacteria of the genus *Staphylococcus*, bacteria of the genus *Escherichia*, bacteria of the genus *Brucella*, and bacteria of the genus *Salmonella*.

In one or more embodiments, the bacteria are resistant to at least one antibiotic selected from the group consisting of a beta-lactam antibiotic, a tetracycline, a colistin, and a vancomycin.

In one or more embodiments, the beta-lactam antibiotic is selected from the group consisting of a methicillin, an oxacillin, a nafcillin, a penicillin, a cephamycin, a carbapenemtetracycline, and any combination thereof.

In one or more embodiments, the composition further comprises at least one antibiotic selected from the group consisting of a methicillin, an oxacillin, a nafcillin, a penicillin, a cephamycin, a carbapenemtetracycline, a cephalosporin, a carbepenem, other beta-lactam antibiotics, a tetracycline, a colistin, a vancomycin, an aminoglycoside, an amphenicol, an ansamycin, a macrolide, a lincosamide, a glycopeptide, a polypeptide, a chloramphenicol, a quinolone, a fucidin, a sulfonamide, a sulfone, a nitrofuran, a diaminopyrimidine, a trimethoprim, a rifamycin, a streptogramin, a lipopeptide, a ketolide, a polyene, an azole, an echinocandin, and any combination thereof.

According to a third aspect, the present disclosure relates to a method of synthesizing at least one safranal epoxide. The method includes reacting safranal with at least one organic peracid at a temperature of e.g. 15-35° C., or 20-30° C. to thermally epoxidize the safranal to form the at least one safranal epoxide, wherein the at least one safranal epoxide is at least one selected from the group consisting of a compound of formula II and a compound of formula III.

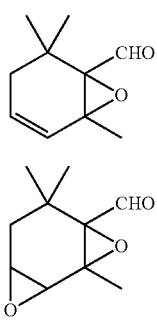

In one or more embodiments, the at least one safranal epoxide is the compound of formula I, and the method further comprises reacting the compound of formula II with at least one peroxide in the presence of light to photochemically epoxidize the compound of formula II to form the compound of formula III.

According to a fourth aspect, the present disclosure relates to a method of synthesizing at least one safranal epoxide. The method includes reacting safranal with at least one peroxide in the presence of light to photochemically epoxidize the safranal to form the at least one safranal epoxide, wherein the at least one safranal epoxide is at least one selected from the group consisting of a compound of formula II and a compound of formula III.

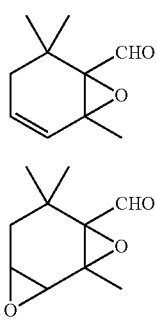

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
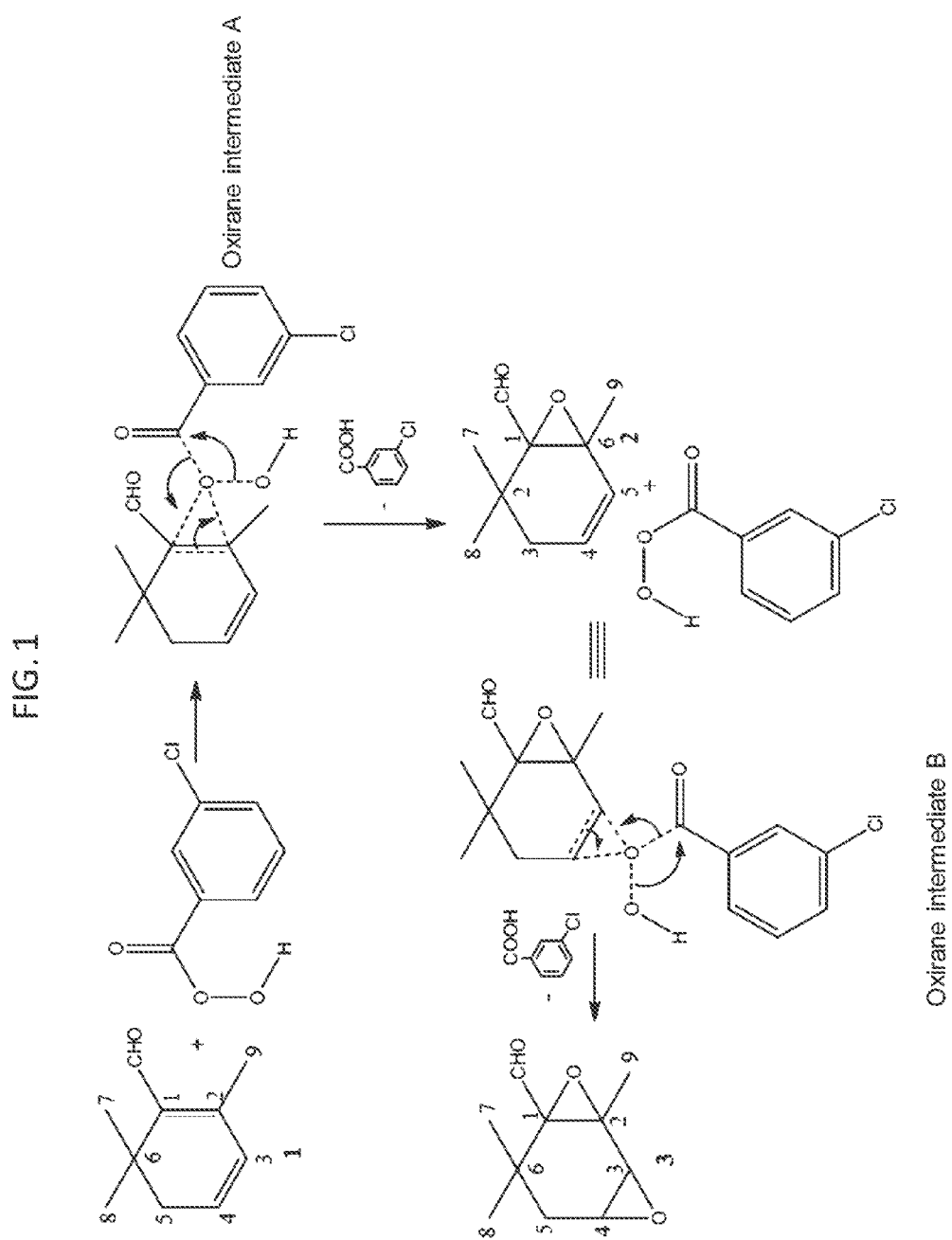
FIG. 1 is a graphical presentation of thermal epoxidation of safranal with m-chloroperbenzoic acid according to Example 1.

According to a first aspect, the present disclosure relates to a method of killing bacteria.

In one embodiment, the method includes contacting the bacteria with an effective amount of safranal of formula (1).

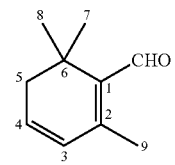

In another embodiment, the method includes contacting the bacteria with an effective amount of at least one oxidation product of safranal selected from the group consisting of a compound of formula II, a compound of formula III, and stereoisomers thereof. The at least one oxidation product of safranal may be one or a mixture of any possible stereoisomers, including any possible diastereomers and/or enantiomers.

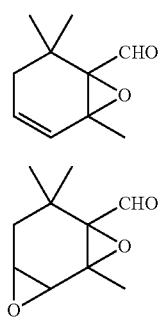

In a preferred embodiment, the oxidation product of safranal is a compound of formula II.

In another preferred embodiment, the oxidation product of safranal is a compound of formula III.

In another preferred embodiment, the oxidation product of safranal is a combination of the compound of formula II and the compound of formula III. The weight percent ratio of the compound of formula II:the compound of formula III may vary without limitation, depending on, for example, the availability of the compounds, the condition of the killing of the bacteria (e.g. temperature, pressure, and the medium containing the bacteria) that may affect the solubility and stability of the compounds, and the strains of the bacteria that may have different sensitivities to the compounds. In some embodiments, the weight percent ratio of the compound of formula II:the compound of formula III is (20-80):(80-20), (30-70):(70-30), (40-60):(60-40), or 50:50.

Safranal may be extracted from *Crocus sativus* with, for example, petroleum ether, petroleum benzene, alcohol (e.g. methanol or ethanol), or a mixture of alcohol and water, or may be obtained in a purified form from a commercial source.

In one embodiment, the compound of formula II and/or the compound of formula III are synthesized by reacting safranal with at least one organic peracid. Non-limiting examples of suitable organic peracids include perbenzoic acid, haloperbenzoic acid (e.g. m-chloroperbenzoic acid), perphthalic acid, and a per(lower alkanoic) acid having six carbon atoms or less in the molecule. The reaction is preferably performed thermally at ambient or room temperature (e.g. 15-35° C., or 20-30° C.) and in a nitrogen atmosphere to yield the compound of formula II, or the compound of formula III, or both the compound of formula II and the compound of formula III, depending on the abundance of the organic peracid(s) relative to safranal and the duration of the reaction, and thus the extent of the oxidation of safranal. In some embodiments, when both the compound of formula II and the compound of formula III are produced, the weight ratio of the compound of formula II:the compound of formula III is in the range of 4:1-1:4, 3:1-1:3, 2:1-1:2, or 1:1, and the overall yield of the compound of formula II and the compound of formula III from the oxidation of safranal with the organic peracid(s) is 50-90%, 60-80%, or 70%. In other embodiments, the compound of formula III is produced by reacting the compound of formula II with one or more organic peracids, for example, m-chloroperbenzoic acid. When the compound of formula II and the compound of formula III are co-present in the reaction mixture, the compound of formula II may be separated from the compound of formula III using a method disclosed in Oxidation Studies on Some Natural Monoterpenes: Citral, Pulegone and Camphene, E. M. Elgendy, and Suzan A. Khayyat, Russian journal of organic chemistry, 44 (6), 814-822, (2008), incorporated herein by reference in its entirety.

In another embodiment, the compound of formula II and/or the compound of formula III are synthesized by reacting safranal with at least one peroxide photochemically in the presence of light, preferably visible light at a wavelength of 390-700 nm, 450-650 nm, 550-650 nm, or 500-600 nm. The at least one peroxide may be one or more inorganic peroxides, such as hydrogen peroxide, peroxymonosulfuric acid (H$_2$SO$_5$), peroxides of the alkali and alkaline earth metals, and peroxides of transition metals, and/or may be one or more organic peroxides, such as acetone peroxide, methyl ethyl ketone peroxide (MEKP), benzoyl peroxide, and the organic peroxides of the general formula below

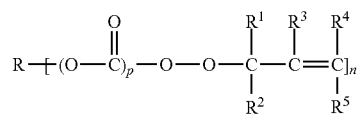

disclosed in EP0273990 A1, incorporated herein by reference in its entirety. In a preferred embodiment, the light is provided by a low-pressure sodium lamp or a high-pressure sodium lamp as a light source. The photochemical reaction is preferably performed at a temperature of from −10° C. to 10° C., from −5° C. to 5° C., from −3° C. to 3° C., or more preferably 0° C. and in a nitrogen atmosphere. Depending on the abundance of the peroxide(s) relative to safranal and the duration of the reaction, and thus the extent of the oxidation of safranal, the reaction may produce the compound of formula II, or the compound of formula III, or both the compound of formula II and the compound of formula III. In some embodiments, when both the compound of formula II and the compound of formula III are produced, the weight percent ratio of the compound of formula II:the compound of formula III lies in the range of 4:1-1:4, 3:1-1:3, 2:1-1:2, or 1:1, and the overall yield of the compound of formula II and the compound of formula III from the oxidation of safranal with the proxide(s) is 30-80%, 40-70%, or 50-60%. In other embodiments, the compound of formula III is produced by reacting the compound of formula II with peroxide(s) in the presence of light. When the compound of formula II and the compound of formula III are co-present in the reaction mixture, the compound of formula II may be separated from the compound of formula III using a method disclosed in The Potential Biologically Active Epoxide, Hydroperoxide and Endoperoxide Derivatives Drived from Natural Monoterpene A-Myrecene, E M Elgendy, Australian Journal of Basic and Applied Sciences 2 (2), 221-224, 2008, incorporated herein by reference in its entirety.

The disclosed oxidation product of safranal is contemplated to be used to kill any type or strain of bacteria, which may be Gram positive bacteria, Gram negative bacteria, antibiotic sensitive bacteria, or antibiotic resistant bacteria. Non-limiting examples of the target bacteria of the oxidation product of safranal include bacteria of the genus *Proteus* (e.g. *Proteus vulgaris*), bacteria of the genus *Klebsiella* (e.g. *Klebsiella pneumonia*), bacteria of the genus *Bacillus* (e.g. *Bacillus subtilis*), bacteria of the genus *Pseudomonas* (e.g. *Pseudomonas aeruginosa*), bacteria of the genus *Staphylococcus* (e.g. *Staphylococcus aureus, Staphylococcus epidermidis*, and *Staphylococcus saprophyticus*), bacteria of the genus *Escherichia* (e.g. *Escherichia coli*), bacteria of the genus *Brucella* (e.g. *Brucella melitensis*), and bacteria of the genus *Salmonella* (e.g. *Salmonella enterica* and *Salmonella bongori*). The oxidation product of safranal may be used to kill bacteria that are resistant to antibiotics that include, but are not limited to, a beta-lactam antibiotic (e.g. a methicillin, an oxacillin, a nafcillin, a penicillin, a cephamycin, a carbapenemtetracycline), a tetracycline, a colistin, and a vancomycin. The effective amount of the oxidation product of safranal for killing the bacteria may vary without limitation, depending on, for example, the type or strain of the bacteria, the type, purity, and stability of the oxidation product of safranal in a particular bacteria killing operation, the medium in which the oxidation product of safranal contacts the bacteria (e.g. oil, gel, or an aqueous solution), the condition of the contacting (e.g. temperature and factors that affect the degree of mixing of the oxidation product of safranal with the bacteria, such as the speed of an agitator performing the mixing, the dispersion level of the bacteria in the mixture of the oxidation product of safranal and the bacteria, and the overall efficiency of the contacting of the bacteria with the oxidation product of safranal), and the desirable bacteria killing rate (e.g. 80%, 90%, 95%, or 100% of the bacteria killed). In some embodiments, the bacteria are present in a liquid or a solid medium, and the effective amount of the oxidation product of safranal lies in the range of 0.1-100, 0.5-90, 1-80, 5-70, 10-60, 20-50, or 30-40 mg/ml liquid or solid medium.

The rate of bacteria killing by the oxidation product of safranal may be quantified by determining the number of bacteria before and following the contacting of the bacteria with the oxidation product of safranal. The number of the bacteria can be determined and reported as CFU, or colony forming units. One colony is formed by a single bacterium when the bacteria are plated at a suitable dilution for single colony formation. This is a standard technique known to microbiologists. Alternatively, when the bacteria are present and are contacted with the oxidation product of safranal in a liquid medium, the number of the bacteria is proportional to and thus may be quantified by optical density (OD) at a wavelength of 590-610 nm, or 600 nm.

Contacting the bacteria with the oxidation product of safranal may be achieved by, without limitation, spraying a solution of the oxidation product of safranal onto the bacteria, mixing the oxidation product of safranal or a solution thereof with the bacteria or a medium containing the bacteria, diffusing the oxidation product of safranal among the bacteria (e.g. by contacting a filter paper containing the oxidation product of safranal with a bacterial lawn grown on an agar medium in a petri dish, the oxidation product of safranal contacts the bacteria by diffusing from the filter paper into the bacterial population), or soaking the bacteria or an object contaminated with the bacteria in a solution of the oxidation product of safranal, wiping a solid surface contaminated with the bacteria with a cloth or a piece of paper impregnated with a solution of the oxidation product of safranal, or covering the bacteria with the solids or powders of the oxidation product of safranal. The time for the contacting may vary without limitation, depending on, for example, the efficiency of the contacting, the sensitivity of the bacteria to the oxidation product of safranal, the initial number of the bacteria, the amount of the oxidation product of safranal the bacteria come in contact with, and the desirable killing rate of the bacteria.

In one embodiment, the bacteria are killed by being contacted concurrently with a combination of one or more oxidation products of safranal and at least one antibiotic selected from the group consisting of a methicillin, an oxacillin, a nafcillin, a penicillin, a cephamycin, a carbapenemtetracycline, a cephalosporin, a carbepenem, other beta-lactam antibiotics, a tetracycline, a colistin, a vancomycin, an aminoglycoside, an amphenicol, an ansamycin, a macrolide, a lincosamide, a glycopeptide, a polypeptide, a chloramphenicol, a quinolone, a fucidin, a sulfonamide, a sulfone, a nitrofuran, a diaminopyrimidine, a trimethoprim, a rifamycin, a streptogramin, a lipopeptide, a ketolide, a polyene, an azole, an echinocandin, and any combination thereof.

In some embodiments, the antibiotics selected for the combination are ones that the bacteria are sensitive to, and the bacteria killing effect of the combination is additive, or preferably synergistic as compared to the bacteria killing effect of the oxidation products of safranal or the antibiotics when either are contacted with the bacteria individually or separately in the absence of the other. "Additive" means a biological effect created from the application of two or more (types of) agents to produce a biological effect that is equal to the sum of the biological effects produced by the application of the individual (type of) agents. "Synergistic" means a biological effect created from the application of two or more (types of) agents to produce a biological effect that is greater than the sum of the biological effects produced by the application of the individual (type of) agents. When the combination of the oxidation products of safranal and the antibiotics produces an additive, or more preferably a synergistic bacteria killing effect, contacting the bacteria concurrently with the combination of the oxidation products of safranal and the antibiotics may advantageously reduce the amounts of both the oxidation products of safranal and the antibiotics needed as compared to the amounts when the oxidation products of safranal or the antibiotics are contacted with the bacteria individually to achieve the same bacteria kill rate. For example, the amount of the oxidation products of safranal or the antibiotics in the combination may be 10-90%, 20-80%, 30-70%, 40-60%, or 50% of the corresponding amount of the oxidation products of safranal or the antibiotics used individually to achieve the same bacteria killing rate. Alternatively, when the combination of the oxidation products of safranal and the antibiotics produces an additive or synergistic bacteria killing effect, contacting the bacteria concurrently with the oxidation products of safranal/antibiotics combination may advantageously result in a higher bacteria killing rate (e.g. 10-100%, 20-90%, 30-80%, 40-70%, or 50-60% higher) as compared to the bacteria killing rate when the bacteria are contacted with the same amount of the oxidation products of safranal or the antibiotics individually.

In other embodiments, the antibiotics selected for the combination are ones that the bacteria are resistant to, such as a beta-lactam antibiotic (e.g. a methicillin, an oxacillin, a nafcillin, a penicillin, a cephamycin, a carbapenemtetracycline), a tetracycline, a colistin, and/or a vancomycin mentioned above. While contacting the bacteria with the antibiotics that the bacteria are resistant to in the absence of the oxidation products of the safranal results in no bacteria killing, in a preferred embodiment, contacting the bacteria concurrently with the combination of the oxidation products of safranal and the antibiotics that the bacteria are resistant to produces a synergistic bacteria killing effect, such that a reduced amount of the oxidation products of safranal is needed in the presence of an amount of the antibiotics (sufficient to potentiate the bacteria killing effect of the oxidation products of safranal) as compared to the amount of the oxidation products of safranal contacting the bacteria in the absence of the antibiotics to achieve the same bacteria killing rate. For example, the reduced amount of the oxidation products of safranal in combination with the antibiotics may be 10-90%, 20-80%, 30-70%, 40-60%, or 50% of the amount of the oxidation products of safranal contacting the bacteria in the absence of the antibiotics to achieve the same bacteria killing rate.

According to a second aspect, the present disclosure relates to a method of preventing or treating an infection of bacteria in a subject who is suffering from or susceptible to bacterial infection.

In one embodiment, the method includes administering to the subject an effective amount of a composition comprising safranal of formula 1 to prevent, inhibit, or reduce a growth of the bacteria.

1

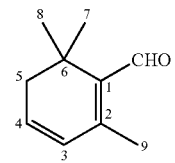

In another embodiment, the method includes administering to the subject an effective amount of a composition comprising at least one oxidation product of safranal selected from the group consisting of a compound of formula II, a compound of formula III, and stereoisomers thereof to prevent, inhibit, or reduce a growth of the bacteria. The at least one oxidation product of safranal may be one or a mixture of any possible stereoisomers, including any possible diastereomers and/or enantiomers.

The oxidation products of safranal of formula II and III have the same characteristics and methods of synthesis as described in the first aspect of the disclosure.

In a preferred embodiment, the oxidation products of safranal of formula II and III are synthesized by reacting safranal with m-chloroperbenzoic acid. A probable mechanism for the formation of the oxidation products of safranal of formula II and III is believed to involve one oxirane intermediate (A) and elimination of m-chlorobenzoic acid molecule to form the product of formula II or two oxirane intermediates (A and B) to form the product of formula III.

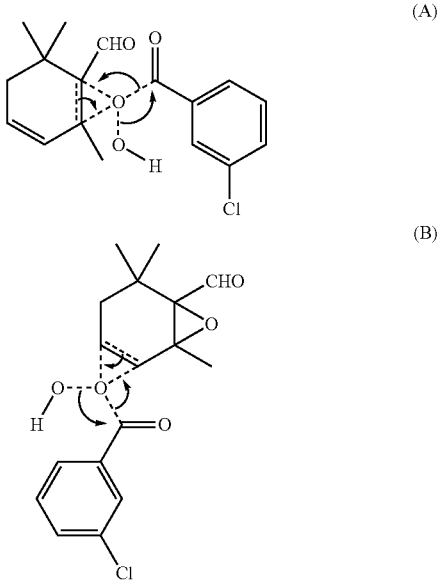

In one embodiment, the subject is a human. In another embodiment, the subject is an animal, such as a domestic animal, e.g. a cat, or a dog, or a farm animal, e.g. a sheep, a cattle, a chicken, or a pig. The bacterial infection may be present on the skin, in the blood, and/or an internal organ (e.g. lung, brain, kidney, or bladder) of the subject. The subject may be diagnosed with a bacterial infection and may have a competent, compromised, or deficient immune function. Alternatively, the subject may not presently have a bacterial infection, but may be susceptible to a bacterial infection due to a compromised or deficient immune function resulting from a disease (e.g. HIV/AIDS) or a medication (e.g. an immunosuppressant drug). The administration of the composition comprising the oxidation product of safranal in an effective amount to the subject may advantageously prevent or treat the bacterial infection through prevention, inhibition, or reduction of the growth of the bacteria at least by the action of the oxidation product of safranal in the composition.

The composition comprising the oxidation product of safranal is contemplated to prevent, inhibit, or reduce the growth of any type of bacteria, particularly pathogenic bacteria causing the bacterial infection. Non-limiting examples of the (pathogenic) bacteria of which growth may be prevented, inhibited, or reduced by the composition comprising the oxidation product of safranal include bacteria of the genus *Proteus* (e.g. *Proteus vulgaris*), bacteria of the genus *Klebsiella* (e.g. *Klebsiella pneumonia*), bacteria of the genus *Bacillus* (e.g. *Bacillus subtilis*), bacteria of the genus *Pseudomonas* (e.g. *Pseudomonas aeruginosa*), bacteria of the genus *Staphylococcus* (e.g. *Staphylococcus aureus, Staphylococcus epidermidis*, and *Staphylococcus saprophyticus*), bacteria of the genus *Escherichia* (e.g. *Escherichia coli*), bacteria of the genus *Brucella* (e.g. *Brucella melitensis*), and bacteria of the genus *Salmonella* (e.g. *Salmonella enterica* and *Salmonella bongori*). The bacteria causing the infection may be sensitive or resistant to antibiotics that include, but are not limited to, a beta-lactam antibiotic (e.g. a methicillin, an oxacillin, a nafcillin, a penicillin, a cephamycin, and a carbapenemtetracycline), a tetracycline, a colistin, and a vancomycin.

In a preferred embodiment, the composition further comprises at least one pharmaceutically, cosmetically, and/or dietarily acceptable excipient or carrier so that the composition comprising the oxidation product of safranal can be administered to the subject as a medication (e.g. an eye drop product, an intravenous fluid, a pill, or a capsule), as a cosmetic product (e.g. a skin care lotion or cream, a perfume, a hair or body care lotion or shampoo, a mouth care solution, a toothpaste, and a soap), as a feed for animals, or as a food or beverage product (e.g. flour, bakery products, pasta/noodle products, cooking oil, confection products, dairy products, tea, vegetable juices, fruit juices, and alcoholic drinks). When the composition comprises the oxidation product of safranal and acceptable pharmaceutical, cosmetic, and/or dietary excipients or carriers, the composition may be in a form of a solution, a spray, a beverage, a tablet, a gel, a paste, a lotion, a cream, a capsule, a powder, and a lozenge, and the composition may be administered intravenously, intradermally, intraperitoneally, orally, by inhalation, transdermally (topical), subcutaneously, and/or transmucosally, depending on, for example, the site of the bacterial infection, and the stability and bioavailability of the oxidation product of safranal in the composition following various routes of administration. For example, a topical administration of the composition in the form of a solution, a gel, a paste, a cream, or a powder may be appropriate for a skin bacterial infection, whereas an oral administration of the composition in the form of a tablet, a capsule, a medicinal syrup, or a beverage, or an intravenous injection of the composition in the form of an intravenous fluid may be appropriate to treat bacterial infection in an internal organ (e.g. throat or lung). The dose and frequency of the administration of the composition to reach an effective amount for preventing or treating the bacterial infection may vary without limitation, depending on, for example, the species, age, weight, size, sex, and physical and medical conditions (e.g. the immune function, and the tolerance of the composition) of the subject, the particular type and the amount/concentration of the oxidation product of safranal in the composition, the route of the administration, the absorption, distribution, metabolism, and excretion of the oxidation product of safranal in the body of the subject, the location and severity of the bacterial infection, and the type of bacteria causing the infection and the bacteria sensitivity to the oxidation product of safranal. In some embodiments, the composition comprising the oxidation product of safranal is administered to a human subject in an effective amount that contains 0.1-15, 1-12, 3-10, 5-8 mg of the oxidation product of safranal/kg body weight of the human subject/day. A skilled artisan is able to determine the effective dose and frequency of the administration of the composition based on the above mentioned factors and other considerations.

In another preferred embodiment, the composition further comprises one or more antibiotics selected from the group consisting of a methicillin, an oxacillin, a nafcillin, a penicillin, a cephamycin, a carbapenemtetracycline, a cephalosporin, a carbepenem, other beta-lactam antibiotics, a tetracycline, a colistin, a vancomycin, an aminoglycoside, an amphenicol, an ansamycin, a macrolide, a lincosamide, a glycopeptide, a polypeptide, a chloramphenicol, a quinolone, a fucidin, a sulfonamide, a sulfone, a nitrofuran, a diaminopyrimidine, a trimethoprim, a rifamycin, a streptogramin, a lipopeptide, a ketolide, a polyene, an azole, an echinocandin, and any combination thereof. The (pathogenic) bacteria causing the bacterial infection may be sensitive or resistant to the antibiotics in the composition.

In a preferred embodiment, the bacteria are sensitive to the antibiotics selected, and co-administration of the oxidation product of safranal and the antibiotics by combining the oxidation product of safranal and the antibiotics in the composition produces an additive or, more preferably, a synergistic bacteria killing effect, as compared to the bacteria killing effect achieved by administration of a composition comprising the oxidation product of safranal without the antibiotics or the antibiotics without the oxidation product of safranal. When the administration of the composition comprising the combination of the oxidation product of safranal and the antibiotics that the bacteria are sensitive to results in an additive or synergistic bacteria killing effect, the amount of both the oxidation product of safranal and the antibiotics in the oxidation product of safranal/antibiotics combination composition may be reduced as compared to the amount when the oxidation product of safranal or the antibiotics are administered individually to achieve the same bacteria killing rate or effect. In some embodiments, the amount of the oxidation product of safranal or the antibiotics in the oxidation product of safranal/antibiotics combination composition is 10-90%, 20-80%, 30-70%, 40-60%, or 50% of the corresponding amount of the oxidation product of safranal or the antibiotics administered individually to achieve the same bacteria killing rate.

In another preferred embodiment, the bacteria are resistant to the antibiotics selected, and co-administration of the oxidation product of safranal and the antibiotics by combining the oxidation product of safranal and the antibiotics in the composition produces a synergistic bacteria killing effect as compared to administration of the antibiotics without the oxidation product of safranal (which leads to no bacteria killing) and administration of the composition comprising the oxidation product of safranal without the antibiotics. When there is a synergy between the oxidation product of safranal and the antibiotics that the bacteria are resistant to, the amount of the oxidation product of safranal in the oxidation product of safranal/antibiotics combination composition may be reduced as compared to the amount of the oxidation product of safranal in a similar composition without the antibiotics to achieve the same bacteria killing rate or effect. In some embodiments, the amount of the oxidation product of safranal in the oxidation product of safranal/antibiotics combination composition is 10-90%, 20-80%, 30-70%, 40-60%, or 50% of the amount of the oxidation product of safranal in the similar composition without the antibiotics to achieve the same bacteria killing rate.

Having generally described this invention, a further understanding can be obtained by reference to certain specific examples which are provided herein for purposes of illustration only and are not intended to be limiting unless otherwise specified.

Example 1

Synthesis of the Compounds of Formula II and Formula III by Thermal Epoxidation of Safranal with m-Chloroperbenzoic Acid Ten mmol of m-chloroperbenzoic acid in an 80% m-chloroperbenzoic acid solution was carefully added in a dropwise manner over a period of 15 min to a solution containing 5 mmol of safranal (compound 1: 2,6,6-trimethylcyclohexa-1,3-diene-1-carbaldehyde) in 25 ml of chloroform at 0° C. The reaction mixture was stirred at room temperature under nitrogen, with the progress of the reaction being monitored by TLC and peroxide test with a 10% KI solution. The mixture was then carefully washed three times with a saturated $NaHCO_3$ aqueous solution (10 ml for each wash) and three times with distilled water (10 ml for each wash). The organic layer was separated, dried over anhydrous $Na_2SO_4$, and evaporated under a reduced pressure at room temperature. The residue was subjected to column chromatography on a silica gel using petroleum ether (bp 60-80° C.)-ethyl acetate (9:2) as eluent to isolate 0.52 g of a mixture of compound 2 of formula II (2,2,6-trimethyl-7-oxabicyclo [4.1.0]-hept-4-ene-1-carbaldehyde) and compound 3 of formula III (2,5,5-trimethyl-3,8-dioxatricyclo[5.1.0.02,4]octane-4-carbaldehyde). Compound 2 and compound 3 in the mixture were separated in pure forms using a method disclosed in Oxidation Studies on Some Natural Monoterpenes: Citral, Pulegone and Camphene, E. M. Elgendy, and Suzan A. Khayyat, Russian journal of organic chemistry, 44 (6), 814-822, (2008), incorporated herein by reference in its entirety. The weight percent ratio of compound 2:compound 3 in the mixture was 65%:35%, and the overall yield was 70%. The thermal epoxidation reaction depicted in FIG. 1 probably involves formation of one oxirane intermediate (i.e. Oxirane intermediate A) and elimination of one m-chlorobenzoic acid molecule to form compound 2, and formation of two oxirane intermediates (i.e. Oxirane intermediate A and Oxirane intermediate B) and elimination of two m-chlorobenzoic acid molecules to form compound 3.

Example 2

Figure 2:
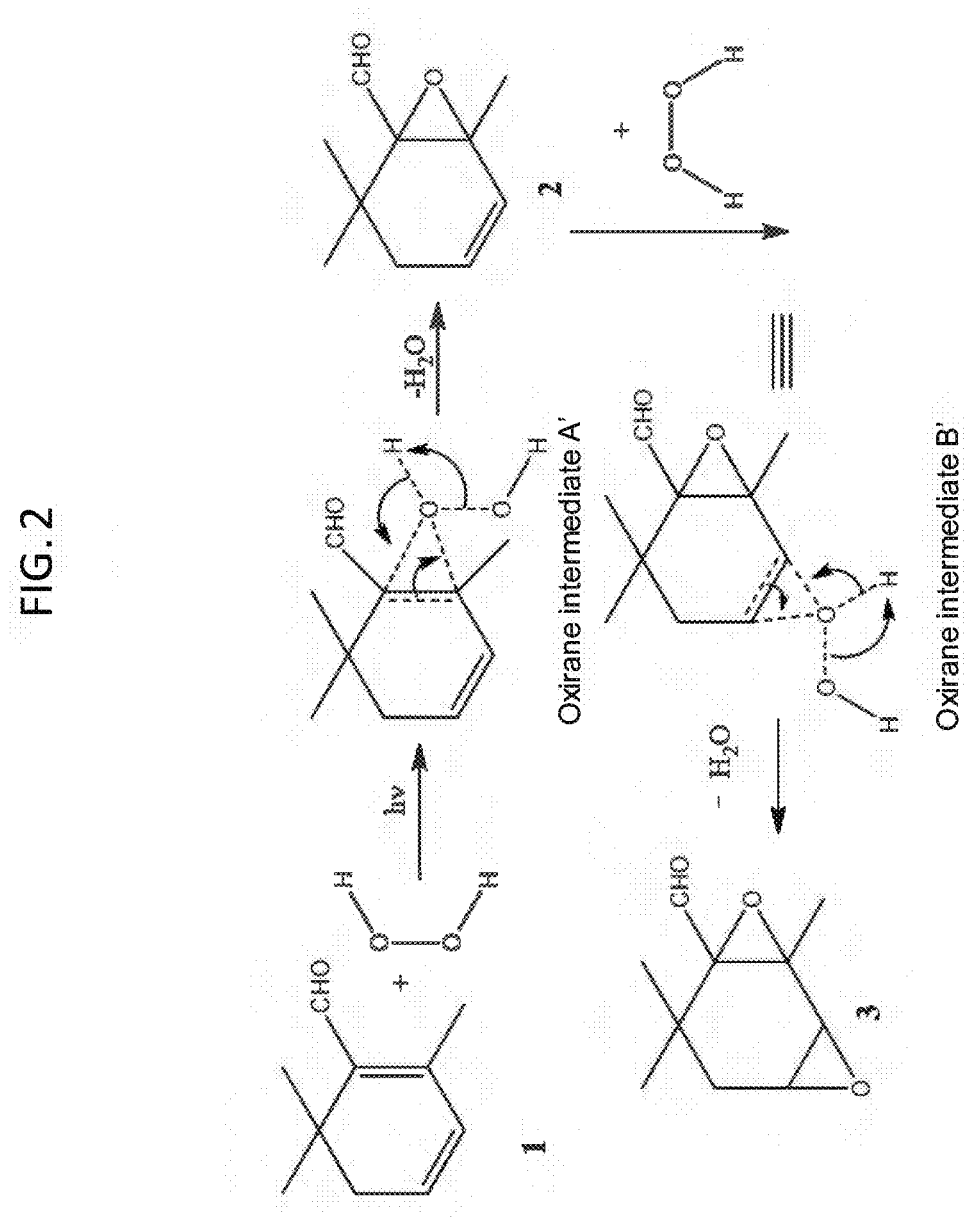
FIG. 2 is a graphical presentation of photochemical epoxidation of safranal with hydrogen peroxide according to Example 2.

Synthesis of the Compounds of Formula II and Formula III by Photochemical Epoxidation of Safranal with Hydrogen Peroxide 2.5 ml of a 30% hydrogen peroxide solution was carefully added dropwise over a period of 5 min to a solution containing 5 mmol of safranal (compound 1) in 25 ml of ethanol under stirring at 0° C. The mixture was irradiated by a sodium lamp for 50 h under nitrogen at 0° C. The mixture was then evaporated under a reduced pressure at room temperature. The resulting gummy residue was treated with 25 ml of chloroform, and the extract was dried over anhydrous sodium sulfate and evaporated under a reduced pressure. The resulting residue was subjected to column chromatography on a silica gel using petroleum ether (bp 60-80° C.)-ethyl acetate (9:2) as eluent to isolate 0.16 g of a mixture of compound 2 of formula II and compound 3 of formula III. Compound 2 and compound 3 in the mixture were separated in pure forms using a method disclosed in The Potential Biologically Active Epoxide, Hydroperoxide and Endoperoxide Derivatives Drived from Natural Monoterpene â-Myrecene, E M Elgendy, Australian Journal of Basic and Applied Sciences 2 (2), 221-224, 2008, incorporated herein by reference in its entirety. The weight percent ratio of compound 2:compound 3 in the mixture was 65%: 35%, and the overall yield was 50%. The photochemical epoxidation reaction depicted in FIG. 2 probably involves formation of one oxirane intermediate (i.e. Oxirane intermediate A') and elimination of one water molecule to form compound 2, and formation of two oxirane intermediates (i.e. Oxirane intermediate A' and Oxirane intermediate B') and elimination of two water molecules to form compound 3.

Example 3

Determination of the Chemical Structures and GC-MS Characterization of Safranal (Compound 1), Compound 2 of Formula II, and Compound 3 of Formula III 1. Safranal (compound 1: 2,6,6-trimethylcyclohexa-1,3-diene-1-carbaldehyde), colorless oil, $C_{10}H_{14}O$ (M 150.21).

$^1$HNMR spectrum of safranal (compound 1) showed three singlet signals for nine protons on three methyl groups 7, 8 and 9 at δ 1.19, 1.19 and 2.17, respectively, a double doublet signal for two protons at position 5 at δ 2.15, a doublet signal for proton 3 at δ 5.93, a double triplet signal for proton 4 at δ 6.16, and a singlet signal for aldehydic proton at δ 10.14. The detailed $^1$HNMR spectrum data of safranal (compound 1) are as follows: δ, ppm: 1.19 s (6H, $C^{7,8}H_3$), 2.15 d.d (2H, 5-H, J=11.14 Hz), 2.17 s (3H, $C^9H_3$), 5.93 d (1H, 3-H, J=10 Hz), 6.16 d.t (1H, 4-H, J=5.10 Hz), 10.14 s (1H, CHO).

$^{13}$CNMR spectrum of safranal (compound 1) indicated the presence of signals of the hexadiene carbon atoms at δ 32.3, 40.7, 129.6, 134.1, 137.1, 146.6, and 191.3 representing ($C_6$), ($C_5$), ($C_4$), ($C_3$), ($C_2$), ($C_1$), and (CO), respectively. The detailed $^{13}$CNMR spectrum data of safranal (compound 1) are as follows: δC, ppm: 17.4 ($C_9$), 25.9 ($C_{7,8}$), 32.3 ($C_6$), 40.7 ($C_5$), 129.6 ($C_4$), 134.1 ($C_3$), 137.1 ($C_2$), 146.6 ($C_1$), 191.3 (CO).

Using GC-MS, safranal (compound 1) was characterized by a retention time of 13.2 min, and a molecular ion peak with the mass-to-charge ratio (m/z) of 150.21 on its mass spectrum. The detailed GC-MS data of safranal (compound 1) are as follows: retention time 13.2 min; m/z (Irel, %): 150 (70) [M]+, 135 (10) [M+-$CH_3$], 121 (80) [M+-$C_2H_5$], 107 (100) [M+-$C_2H_3O$], 91 (90) [M+-$C_3H_7O$], 79 (15) [M+-$C_4H_7O$], 41 (7) [$C_3H_5$]+.

2. Compound 2 of formula II (2,2,6-trimethyl-7-oxabicyclo [4.1.0]-hept-4-ene-1-carbaldehyde), colorless oil, $C_{10}H_{14}O_2$(M 166.21).

$^1$HNMR spectrum of compound 2 showed three singlet signals for nine protons on three methyl groups 7, 8, and 9 at δ 1, 1.01, and 1.5, respectively, three double doublet signals for protons 3, 3 and 4 at δ 1.84, 2, and 5.6, respectively, a doublet signal for proton 5 at δ 5.7, and a singlet signal for aldehydic proton at δ 9.61. The detailed $^1$HNMR spectrum data of compound 2 are as follows: δ, ppm: 1.00 s (3H, $C^7H_3$), 1.01 s (3H, $C^8H_3$), 1.5 s (3H, $C^9H_3$), 1.84 d.d (1H, 3-H, J=2.8 Hz), 2.00 d.d (1H, 3-H, J=2.8 Hz), 5.6 d.d (1H, 4-H, J=7.8 Hz), 5.7 d (1H, 5-H, J=7 Hz), 9.61 s (1H, CHO).

$^{13}$CNMR spectrum of compound 2 showed the signals of the hexene carbon atoms of ($C_2$), ($C_3$), ($C_6$), (C), ($C_4$), ($C_5$), and (CO) at δ 39, 39.5, 45, 95, 125.8, 132, and 200, respectively. The detailed $^{13}$CNMR spectrum data of compound 2 are as follows: δC, ppm: 19 ($C_9$), 23.6 ($C_7$), 24.0 ($C_8$), 39.0 ($C_2$), 39.5 ($C_3$), 45.0 ($C_6$), 95.0 ($C_1$), 125.8 ($C_4$), 132.0 ($C_5$), 200.0 (CO).

Using GC-MS, compound 2 was characterized by a retention time of 13.93 min and a molecular ion peak with the mass-to-charge ratio (m/z) of 166.21 on its mass spectrum. The detailed GC-MS data of compound 2 are as follows: retention time 13.93 min; m/z (Irel, %): 166 (35) [M]+, 150 (20) [M+-O], 135 (10) [M+-$CH_3O$], 121 (9) [M+-$CHO_2$], 109 (5) [M+-$C_3H_5O$], 95 (50) [M+-$C_3H_3O_2$], 82 (35) [C6H10]+, 70 (48) [C5H10]+; 41 (100) [C3H5]+.

3. Compound 3 of formula III (2,5,5-trimethyl-3,8-dioxatricyclo[5.1.0.02,4]octane-4-carbaldehyde), colorless oil, $C_{10}H_{14}O_3$(M 182.21).

$^1$HNMR spectrum of compound 3 showed three singlet signals for nine protons on three methyl groups 7, 8 and 9 at δ 1, 1.01, and 1.21, respectively, two double doublet signals for protons 3 and 3 at δ 1.31 and 1.6, respectively. Additionally, the $^1$HNMR spectrum showed a complex pattern at δ 2.62 representing proton 4, a doublet signal at δ 3.2 representing proton 5, and a singlet signal at δ 9.62 representing the aldehydic proton. The detailed $^1$HNMR spectrum data of compound 3 are as follows: δ, ppm: 1.00 s (3H, $C^7H_3$), 1.01 s (3H, $C^8H_3$), 1.21 s (3H, $C^9H_3$), 1.31 d.d (1H, 3-H, J=2.8 Hz), 1.60 d.d (1H, 3-H, J=2.8 Hz), 2.62 m (1H, 4-H), 3.2 d (1H, 5-H, J=8 Hz), 9.62 s (1H, CHO).

$^{13}$CNMR spectrum of compound 3 showed the signals of the hexane carbon atoms of ($C_2$), ($C_3$), ($C_4$), ($C_5$), ($C_6$), ($C_1$), and (CO) at δ 26.1, 39.6, 45.1, 67.4, 67.5, 90.9, and 203, respectively. The detailed $^{13}$CNMR spectrum data of compound 3 are as follows: δC, ppm: 24.7 ($C_7$), 24.9 ($C_8$), 26.1 ($C_2$), 30.9 ($C_9$), 39.6 ($C_3$), 45.1 ($C_4$), 67.4 ($C_5$), 67.5 ($C_6$), 90.9 ($C_1$), 203.0 (CO).

Using GC-MS, compound 3 was characterized by a retention time of 16.65 min and a molecular ion peak with the mass-to-charge ratio (m/z) of 182.21 on its mass spectrum. The detailed GC-MS data of compound 3 are as follows: retention time, min: 16.45-16.85; m/z (Irel, %): 183 (10) [M$^+$+1], 182 (6) [M], 166 (5) [M$^+$-O], 150 (3) [M$^+$-$O_2$], 137 (15) [M$^+$-CHO2], 121 (15) [M$^+$-CHO3], 109 (30) [M$^+$-$C_3H_5O_2$], 82 (20) [C6H10]+, 43 (100) [C3H7]+.

Example 4

Figure 3B:
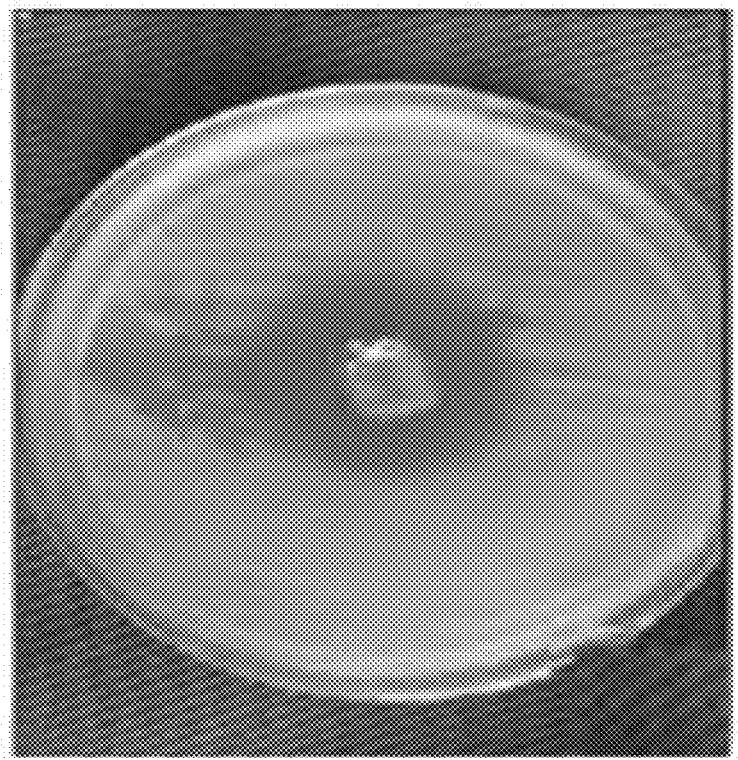
FIG. 3B is a picture showing the presence of an inhibition zone in the bacterial lawn of *Staphylococcus aureus* grown on Mueller Hinton media in a petri dish with the agar well containing test compounds 2 and 3 obtained by the thermal epoxidation of safranal according to Example 4.
Figure 3A:
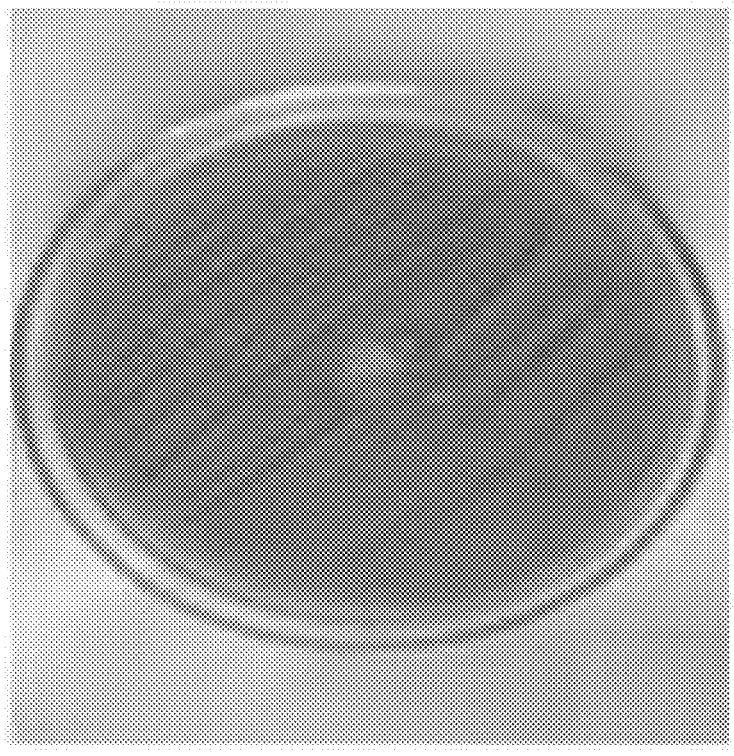
FIG. 3A is a picture showing the absence of an inhibition zone in the bacterial lawn of *Staphylococcus aureus* grown on Mueller Hinton media in a petri dish with the agar well containing no test compound (i.e. the control plate) according to Example 4.
Figure 3D:
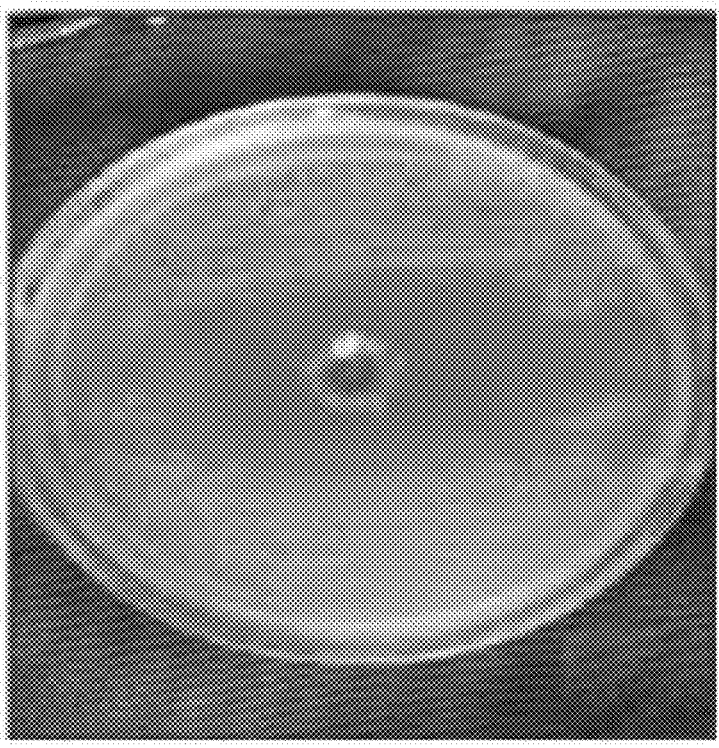
FIG. 3D is a picture showing the presence of an inhibition zone in the bacterial lawn of *Staphylococcus aureus* grown on Mueller Hinton media in a petri dish with the agar well containing safranal according to Example 4.
Figure 3C:
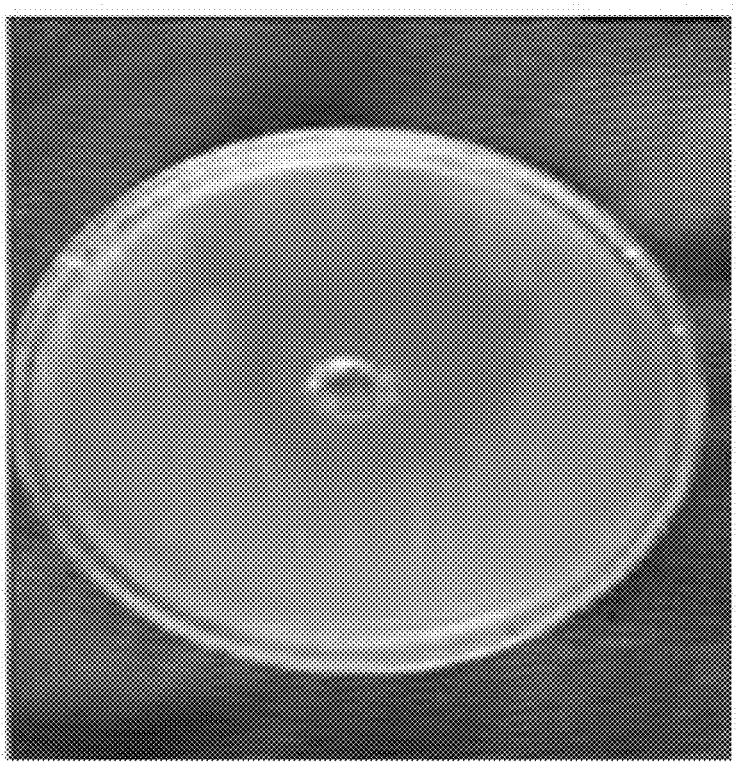
FIG. 3C is a picture showing the presence of an inhibition zone in the bacterial lawn of *Staphylococcus aureus* grown on Mueller Hinton media in a petri dish with the agar well containing test compounds 2 and 3 obtained by the photochemical epoxidation of safranal according to Example 4.

Determination of Antibacterial Activities of Safranal, a Mixture of Compound 2 and Compound 3 Obtained by Thermal Epoxidation of Safranal, and a Mixture of Compound 2 and Compound 3 Obtained by Photochemical Epoxidation of Safranal The antibacterial activities of safranal, a mixture of compound 2 and compound 3 obtained by the thermal epoxidation of safranal according to scheme 1, and a mixture of compound 2 and compound 3 obtained by the photochemical epoxidation of safranal according to scheme 2 against methicillin resistant *Staphylococcus aureus* (MRSA) were determined by the agar well diffusion method described by Collins, C. H., P. M. Lyne, J. M. Grange, Microbial Methods., 6$^{th}$ Edition, Butterworhs Co. Ltd, London; 1989. p. 410, incorporated herein by reference in its entirety. FIG. 3A shows the absence of an inhibition zone in the bacterial lawn of *Staphylococcus aureus* grown on Mueller Hinton media in a control plate where the agar well contained none of the test compounds. FIGS. 3B, 3C, and 3D show the presence of an inhibition zone in the bacterial lawn of *Staphylococcus aureus* grown on Mueller Hinton media in the plates where the agar well contained the mixture of compound 2 and compound 3 obtained by the thermal epoxidation of safranal, the mixture of compound 2 and compound 3 obtained by the photochemical epoxidation of safranal, and safranal, respectively, indicating that all of the above test compounds have an antibacterial activity against methicillin resistant *Staphylococcus aureus*. Table 1 shows the diameter of the inhibition zone in each plate. The plate tested with the mixture of compound 2 and compound 3 obtained by the thermal epoxidation of safranal had an inhibition zone of 35 mm in diameter. The plate tested with the mixture of compound 2 and compound 3 obtained by the photochemical epoxidation of safranal had an inhibition zone of 33 mm in diameter. The plate tested with safranal had an inhibition zone of 27 mm in diameter.

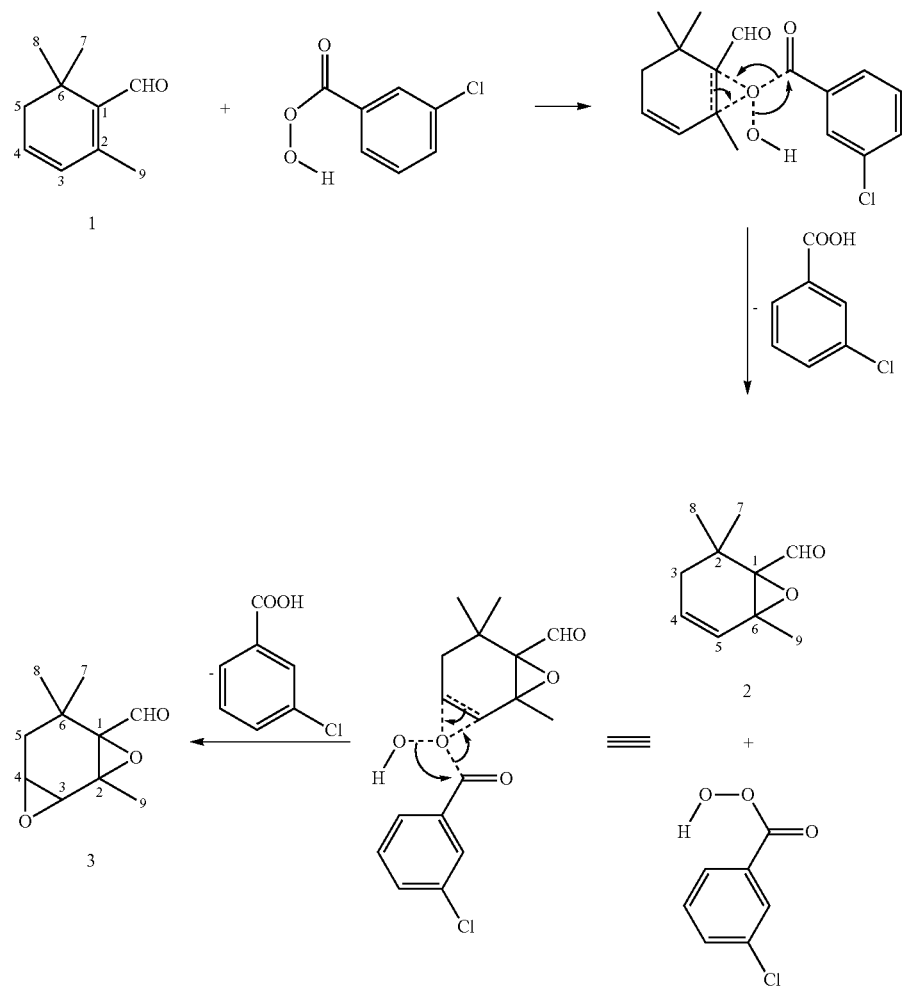

Scheme 1
Thermal Epoxidations with m-Chloroperbenzoic Acid

Scheme 2
Photochemical epoxidation with hydrogen peroxide

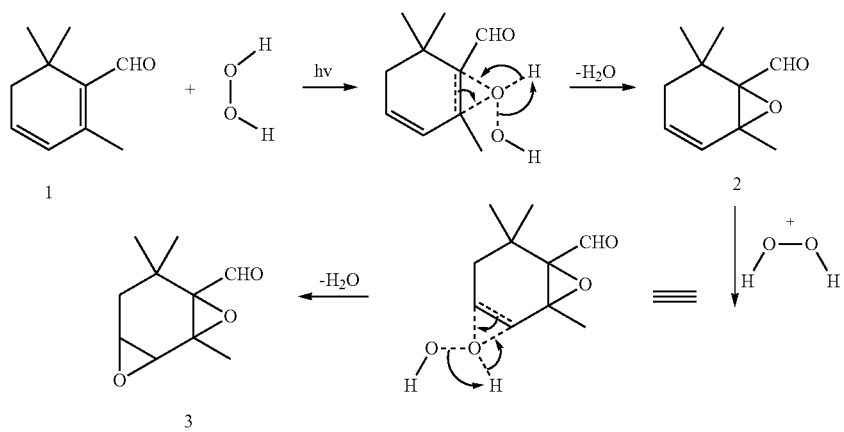

Table 1: Antibacterial Activity (Inhibition Zone Diameter) of the Mixture of Compound 2 and Compound 3 Obtained by the Thermal Epoxidation of Safranal or by the Photochemical Epoxidation of Safranal, and Safranal Against *Staphylococcus aureus* Grown on Mueller Hinton Media Using Agar Well Diffusion Method

| No. | Treatment | Inhibition zone diameter (mm). |
|---|---|---|
| 1 | Control | 0 |
| 2 | Mixture of compound 2 and compound 3 obtained by thermal epoxidation of safranal | 35.00 |
| 3 | Mixture of compound 2 and compound 3 obtained by photochemical epoxidation of safranal | 33.00 |
| 4 | Safranal | 27.00 |

The invention claimed is:

1. A method of synthesizing at least one safranal epoxide, comprising:
reacting safranal with at least one organic peracid at a temperature of 15-35° C. to thermally epoxidize the safranal to form the at least one safranal epoxide, wherein the at least one safranal epoxide is at least one selected from the group consisting of a compound of formula II and a compound of formula III

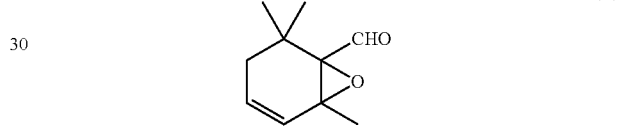

(II)

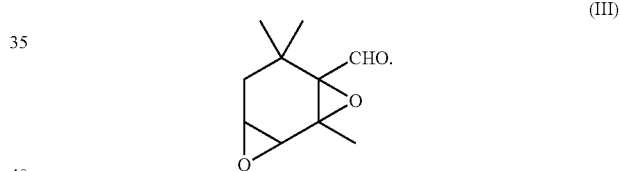

(III)

2. The method of claim 1, wherein the at least one safranal epoxide is the compound of formula II, and
wherein the method further comprises reacting the compound of formula II with at least one peroxide in the presence of light to photochemically epoxidize the compound of formula II to form the compound of formula III.

* * * * *